United States Patent
Chen et al.

(10) Patent No.: US 9,296,692 B2
(45) Date of Patent: Mar. 29, 2016

(54) USE OF INDOLYL AND INDOLINYL HYDROXAMATES FOR TREATING HEART FAILURE OF NEURONAL INJURY

(75) Inventors: Yi-Jen Chen, Taipei (TW); Kuo-Sheng Hung, Taipei (TW); Yu-Hsun Kao, New Taipei (TW); Jing-Ping Liou, Taipei (TW); Pei-Wen Shan, New Taipei (TW)

(73) Assignee: TAIPEI MEDICAL UNIVERSITY, Taipei (TW)

( * ) Notice: Subject to any disclaimer, the term of this patent is extended or adjusted under 35 U.S.C. 154(b) by 43 days.

(21) Appl. No.: 14/345,246

(22) PCT Filed: Sep. 15, 2012

(86) PCT No.: PCT/US2012/055664
§ 371 (c)(1),
(2), (4) Date: Nov. 12, 2014

(87) PCT Pub. No.: WO2013/040520
PCT Pub. Date: Mar. 21, 2013

(65) Prior Publication Data
US 2015/0065552 A1    Mar. 5, 2015

Related U.S. Application Data

(60) Provisional application No. 61/534,902, filed on Sep. 15, 2011, provisional application No. 61/537,589, filed on Sep. 22, 2011.

(51) Int. Cl.
| | |
|---|---|
| *C07D 209/30* | (2006.01) |
| *C07D 209/08* | (2006.01) |
| *C07D 209/18* | (2006.01) |
| *A61K 31/404* | (2006.01) |

(52) U.S. Cl.
CPC ............ *C07D 209/30* (2013.01); *A61K 31/404* (2013.01); *C07D 209/08* (2013.01); *C07D 209/18* (2013.01)

(58) Field of Classification Search
USPC ........................... 514/418, 419; 548/484, 491
See application file for complete search history.

(56) References Cited

U.S. PATENT DOCUMENTS

| | | |
|---|---|---|
| 5,338,755 A | 8/1994 | Wagnon et al. |
| 2008/0269312 A1 | 10/2008 | Herrera et al. |
| 2010/0022514 A1* | 1/2010 | Cho et al. .................. 514/213.01 |
| 2010/0069388 A1 | 3/2010 | Inoue et al. |
| 2011/0245315 A1 | 10/2011 | Chen et al. |

FOREIGN PATENT DOCUMENTS

WO    WO 2006/117165    * 11/2006

OTHER PUBLICATIONS

International Search Report and Written Opinion for PCT/US2012/055664.
Mahboobi et al. 2-Aroylindoles and 2-Aroylbenzofurans with N-Hydroxyacrylamide Substructures as a Novel Series of Rationally Designed Histone Deacetylase Inhibitors, J. Med. Chem., 2007, vol. 50(18), pp. 4405-4418. abstract; p. 4410, Table 4.
Ortore et al. Docking of Hydroxamic Acids into HDAC1 and HDAC8: A Rationalization of Activity Trends and Selectivities, J. Chem. Inf. Model., 2009, 49 (12), pp. 2774-2785. abstract; p. 2778, col. 1, para 2—col. 2, para 3; p. 2779, Table 5; p. 2780, col. 2, para 1—p. 2781, col. 2, para 1; Fig 2.
Bush et al. Protein Acetylation in the Cardiorenal Axis: The Promise of Histone Deacetylase Inhibitors, Circ Res. 2010, vol. 106, pp. 272-284. p. 274, col. 2, para 2-4; p. 275, Fig 2; p. 276, co12, para 2.
Bush, et al.: "Protein Acetylation in the Cardiorenal Axis The Promise of Histone Deacetylase Inhibitors"; vol. 66, pp. 272-284, 2010.
Maliboobi, et al: "2-Aroylindoles and 2-Aroylbenzofurans with N-Hydroxyacrylaminde Substructures as a Novel Series of Rationally Designed Histone Deacetylase Inhibitors"; vol. 50, pp. 4405-4418, 2007.
Zhang, et al.: "HDAC inhibitor incresses histone H3 acetylation and reduces microglia inflammatory response following traumatic brain injury in rats"; vol. 1226, pp. 181-191, 2008.
SIPO Office Action dated May 6, 2015 in corresponding Chinese Application (No. 201280045262.9).
SIPO Search Report dated Apr. 27, 2015.
English translation of search report dated May 6, 2015 in corresponding Chinese Application (No. 201280045262.9).

* cited by examiner

*Primary Examiner* — Shirley V Gembeh
(74) *Attorney, Agent, or Firm* — McClure, Qualey & Rodack, LLP

(57) ABSTRACT

Novel use of small molecules, particularly indolyl and indolinyl hydroxamates is disclosed herein. The indolyl and indolinyl hydroxamates are useful as lead compounds for manufacturing a medicament or a pharmaceutical composition for treating a patient suffering from heart failure or neuronal injury.

5 Claims, 6 Drawing Sheets

USE OF INDOLYL AND INDOLINYL HYDROXAMATES FOR TREATING HEART FAILURE OF NEURONAL INJURY

BACKGROUND OF THE INVENTION

1. Field of the Invention

The present disclosure relates to novel use of small molecules, particularly indolyl and indolinyl hydroxamates. The indolyl and indolinyl hydroxamates are useful as lead compounds for manufacturing a medicament or a pharmaceutical composition for treating a patient suffering from heart failure or neuronal injury.

2. Description of Related Art

Heart failure is a common cardiovascular condition where the heart fails to circulate enough blood and oxygen to meet the needs of other body organs. In developed countries, around 2% of the population suffers from heart failure, with its prevalence increases with age. Heat failure is now the leading cause of hospitalization for individuals older than 65 and is a major contributor to the escalation of heath care costs. Current treatments of heart failure are dedicated to restore the function of the heart by using pharmacological agents, such as the angiotensin converting enzyme (ACE) inhibitors, angiotensin II receptor blockers (ARBs), diuretics, digitalis glycosides, and beta blockers to improve contractile performance. However, common adverse side effects, such as hypotension, renal dysfunction, and impaired physical activity, accompanied by the use of these drugs limit their applications. For terminal heart failure, heart transplantation is an alternative to drug. Yet, the number of available heart donors is limited.

Brain and spinal cord injury caused by stroke, trauma or hypoxia often result in lifelong disability and premature death; accordingly, traumatic brain injury (TBI) and ischemic stroke are two serious public health issues in most countries. An estimated 1.7 million TBI-related deaths, hospitalizations, and emergency department visits occur in the U.S. each year; TBI is a contributing factor to a third (30.5%) of all injury-related deaths in the U.S. or about 52,000 deaths annually. As to ischemic stroke, it is currently the No. 4 killer and a leading cause of long term disability in the U.S. Each year, about 795,000 people suffers a stroke and is the primary cause of about one in every 18 deaths in 2008. Deaths from ischemic stroke are predicted to double between 2000 to 2032. The number of people living with stroke is projected to increase by 25% by 2030, translating into an additional 4 million people with stroke in U.S. alone.

In view of the foregoing, there exist in the related art a need for an agent or a compound that may improve or restore the cardiac functions or reduce or prevent neuronal dysfunction and death after ischemic, hypoxia or traumatic brain injury.

SUMMARY

The present disclosure is based, at least in part, unexpected discovery that the compound having formula (I),

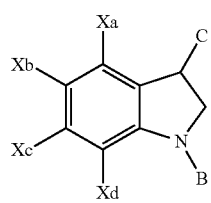

may protect neuron from injury or improve or restore the cardiac functions of a subject such as human, wherein B is R, C(O)R, $CH_2R$, $SO_2R$, $SO_3R$, or $SO_2NRR'$; C is R, C(O)R, $CH_2R$, $SO_2R$, or CH=CHC(O)NHOH; each $X_a$, $X_b$, $X_c$ and $X_d$ are independently R, halogen, nitro, nitroso, OR, or CH=CHC(O)NHOH; and each R and R' are independently H, alkyl, alkenyl, alkynyl, aryl, or heteroaryl. The results of this invention suggest that these active compounds are potential lead compounds for use as therapeutic agents for the treatment of heart failure or neuronal injury. According to embodiments of the present disclosure, heart failure may result from cardiac fibrosis, hypertension, myocardial infarction, myocardial ischaemia, dilated cardiomyopathy, hypertrophic cardiomyopathy, restrictive cardiomyopathy, stress cardiomyopathy, diabetic cardiomyopathy, or idiopathic cardiomyopathy. Neuronal injury may result from traumatic brain injury (TBI) or ischemic stroke.

Accordingly, it is the first aspect of this disclosure to provide a method of treating a subject suffering from heart failure or neuronal injury. The method comprises administering to the subject a therapeutically effective amount of a compound having formula (I):

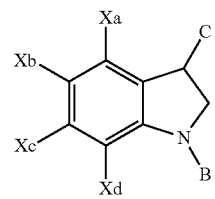

wherein B is R, C(O)R, $CH_2R$, $SO_2R$, $SO_3R$, or $SO_2NRR'$; C is R, C(O)R, $CH_2R$, $SO_2R$, or CH=CHC(O)NHOH; each $X_a$, $X_b$, $X_c$ and $X_d$ are independently R, halogen, nitro, nitroso, OR, or CH=CHC(O)NHOH; and each R and R' are independently H, alkyl, alkenyl, alkynyl, aryl, or heteroaryl. In one example, each C, $X_a$, $X_c$ and $X_d$ are independently H; B is $SO_2R$; and $X_b$ is CH=CHC(O)NHOH.

The subject may be a mammal, preferably a human. The heart failure is caused by cardiac fibrosis, hypertension, myocardial infarction, myocardial ischaemia, dilated cardiomyopathy, hypertrophic cardiomyopathy, restrictive cardiomyopathy, stress cardiomyopathy, diabetic cardiomyopathy, or idiopathic cardiomyopathy. Neuronal Injury may be caused by TBI or ischemic stroke.

In some embodiments, the dose administered to the subject is from about 1 to 100 mg/Kg body weight of the subject by injection, such as intravenous or intramuscular injection. In certain embodiments, the dose is administered to the subject by intravenous injection from about 10 to 100 mg/Kg body weight of the subject, such as 30 mg/Kg body weight of the subject. The dose can be administered in a single aliquot, or alternatively in more than one aliquot.

In some embodiments, the method further comprises administering to the subject an agent that is known to improve or restore the cardiac function(s) before, together with and/or after administering the compound having the formula shown above. Examples of such agent include, but are not limited to, angiotensin converting enzyme (ACE) inhibitors, angiotensin II receptor blockers, diuretics, digitalis glycosides, and beta blockers. In other embodiments, the method further comprises administering to the subject an agent that is known to improve the symptoms of neuronal injury before, together with and/or after administering the compound having the formula shown above. Examples of such agent include, but are not limited to, reactive oxygen scavenger, anticoagulant and the like.

It is therefore the second aspect of this disclosure to provide a use of the compound of formal (I) as described above for manufacturing a medicament or a pharmaceutical composition for treating heart failure or neuronal injury; the medicament or the pharmaceutical composition comprises a therapeutically effective amount of a compound having the formula shown above; and a therapeutically acceptable excipient.

The compound of this invention is present at a level of about 0.1% to 99% by weight, based on the total weight of the pharmaceutical composition. In some embodiments, the compound of this invention is present at a level of at least 1% by weight, based on the total weight of the pharmaceutical composition. In certain embodiments, the compound of this invention is present at a level of at least 5% by weight, based on the total weight of the pharmaceutical composition. In still other embodiments, the compound of this invention is present at a level of at least 10% by weight, based on the total weight of the pharmaceutical composition. In still yet other embodiments, the compound of this invention is present at a level of at least 25% by weight, based on the total weight of the pharmaceutical composition.

In some embodiments, the medicament or the pharmaceutical composition of this invention further includes an agent that is known to improve or restore the function(s) of heart before, together with and/or after administering the compound having the formula shown above. Examples of such agent include, but are not limited to, angiotensin converting enzyme (ACE) inhibitors, angiotensin II receptor blockers, diuretics, digitalis glycosides, beta blockers, direct acting vasodilators and the like. In other embodiments, the method further comprises administering to the subject an agent that is known to improve the symptoms of neuronal injury before, together with and/or after administering the compound having the formula shown above. Examples of such agent include, but are not limited to, reactive oxygen scavenger, anticoagulant and the like.

The details of one or more embodiments of the invention are set forth in the accompanying description below. Other features and advantages of the invention will be apparent from the detail descriptions, and from claims.

BRIEF DESCRIPTION OF THE DRAWINGS

The present description will be better understood from the following detailed description read in light of the accompanying drawings, where.

DESCRIPTION

Figure 1:
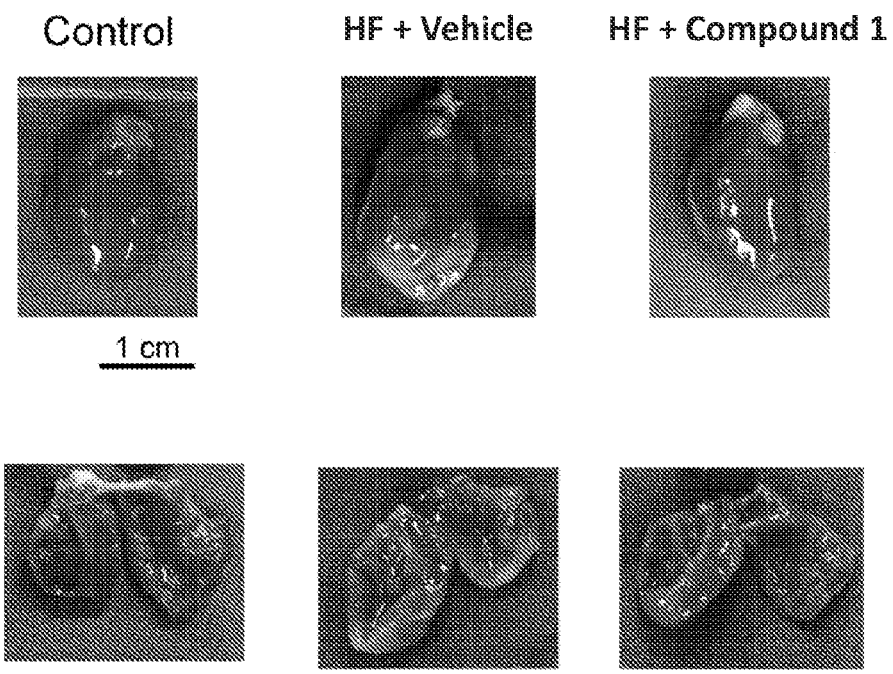
FIG. 1 presents photographs illustrating the cardiac morphology taken from normal rat, heart failure (HF) rat treated with vehicle or compound 1 of this invention in accordance with one example of the present invention.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

The present disclosure is based, at least in part, unexpected discovery that the compound having formula (I) is effective in re-establishing adequate blood circulation in heart tissue or providing neuronal protective activity to a subject,

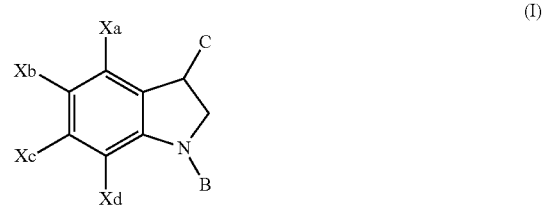

(I)

wherein B is R, C(O)R, CH$_2$R, SO$_2$R, SO$_3$R, or SO$_2$NRR'; C is R, C(O)R, CH$_2$R, SO$_2$R, or CH=CHC(O)NHOH; each X$_a$, X$_b$, X$_c$ and X$_d$ are independently R, halogen, nitro, nitroso, OR, or CH=CHC(O)NHOH; and each R and R' are independently H, alkyl, alkenyl, alkynyl, aryl, or heteroaryl. In one example, each C, X$_a$, X$_c$ and X$_d$ are independently H; B is SO$_2$R; and X$_b$ is CH=CHC(O)NHOH.

Therefore, the compounds of formula (I) are potential lead compounds for use as therapeutic agents for the treatment of heart failure or neuronal injury. The heart failure may be caused by cardiac fibrosis, hypertension, myocardial infarction, myocardial ischaemia, dilated cardiomyopathy, hypertrophic cardiomyopathy, restrictive cardiomyopathy, stress cardiomyopathy, diabetic cardiomyopathy, or idiopathic cardiomyopathy. Further, the compounds of formula (I) are also effective in providing neuronal protective activity to a subject; therefore, these active compounds are potential lead compounds for use as therapeutic agents for the treatment of neuronal injury, such as traumatic brain injury (TBI) or ischemic stroke.

Accordingly, this disclosure provides a method of treating neuronal injury such as traumatic brain injury (TBI) or ischemic stroke by administering to a subject in need thereof an effective amount of the compounds of formula (I).

TBI contributes to substantial number of deaths and cases of permanent disability. Causes include, among others, falls, vehicle accidents, and violence. A TBI is caused by a bump, blow or jolt to the head or a penetrating head injury that disrupts the normal function of the brain. Not all blows or jolts to the head result in TBI. TBI can cause a host of physical, cognitive, emotional, and behavioral effects, and outcome can range from complete recovery to permanent disability or death. Neurobehavioral deficits, especially impaired cognitive function, are often the cause of significant disability after TBI. Hence, compounds that are effective in improving neurobehavioral deficits are potential candidate compounds for manufacturing a medicament or composition for treating TBI.

Ischemic stroke is caused by a decrease of blood supply to part of the brain, and thereby leading to dysfunction of the brain tissue in that area. There are four major reasons ischemic stroke happens, thrombosis (obstruction of a blood vessel by a blood clot forming locally); embolism (obstruction due to an embolus from elsewhere in the body), systemic hypoperfusion (general decrease in blood supply, e.g., in shock) and venous thrombosis. It is known that cerebral ischemia triggers robust phosphorylation of cAMP response element-binding protein (CREB) and CREB-mediated gene expression encoding neuroprotective molecules in neurons (Kitagawa K., FEBS J. 2007 274(13):3210-7); hence compounds effective in activating phosphorylation of CREB are potential lead compounds that may mitigate ischemia stroke.

This disclosure also provides a method of treating heart failure by administering to a subject in need thereof an effective amount of the compounds of formula (1). Heart failure may be those caused by cardiac fibrosis, hypertension, myocardial infarction, myocardial ischaemia, dilated cardiomyopathy, hypertrophic cardiomyopathy, restrictive cardiomyopathy, stress cardiomyopathy, diabetic cardiomyopathy, or idiopathic cardiomyopathy.

Heart failure is a general term and may develop as a complication of various conditions. Conditions that causes heart failure affect the ability of the heart to function well as a pump; exemplary conditions causing heart failure are set forth as follows.

(I) Cardiac fibrosis: Cardiac fibrosis refers to an abnormal thickening of the heart valves due to inappropriate proliferation of cardiac fibroblasts. The thickening, together with the loss of flexibility of cardiac fibroblasts resulted therefrom, eventually may lead to heart failure.

(II) Hypertension: Hypertension is a chronic cardiovascular disease in which the systemic arterial blood pressure is elevated. Hypertension makes it harder for the heart to pump blood because of the increased pressure in the arteries, which, over time, leads to heart failure.

(III) Myocardial infarction: Myocardial infarction (MI) or acute myocardial infarction (AMI), commonly known as a heart-attack, is the death of heart muscle from the sudden blockage of a coronary artery. Severe myocardial infarction may lead to heart failure.

(IV) Myocardial ischaemia: Myocardial ischaemia, or ischemic heart disease (IHD), is a disease characterized by reduced blood supply of the heart muscle, usually due to narrowing of the coronary arteries.

(V) Cardiomyopathy: Cardiomyopathy is a disease of heart muscle (myocardium). It is often associated with inadequate heart pumping that lead to heart failure. Cardiomyopathies could be classified in accordance with the causes thereof. Non-limiting examples of cardiomyopathies include, but are not limited to, dilated cardiomyopathy, hypertrophic cardiomyopathy, restrictive cardiomyopathy, stress cardiomyopathy, diabetic cardiomyopathy, and idiopathic cardiomyopathy. In dilated cardiomyopathy, a portion of the myocardium is dilated; therefore, the heart becomes weakened and enlarged and cannot pump blood efficiently. Hypertrophic cardiomyopathy involves the enlargement and thickening of the heart muscle of the ventricles (lower chambers) which results in a decrease in size of the ventricles. Pathological hypertrophy leads to heart failure, while non-pathological, psychological hypertrophy may not lead to heart failure. Restrictive cardiomyopathy is a form of cardiomyopathy in which the walls are rigid, and the heart is restricted from stretching and filling with blood properly. In time, restrictive cardiomyopathy patients develop diastolic dysfunction and eventually heart failure. Stress cardiomyopathy, or stress-induced cardiomyopathy, is a type of non-ischemic cardiomyopathy in which there is a sudden temporary weakening of the myocardium, which is a well-recognized cause of acute heart failure. Diabetic cardiomyopathy is a disorder of the heart muscle in people with diabetes. It can lead to inability of the heart to circulate blood through the body effectively, a state known as heart failure. Other cardiomyopathies may also lead to heart failure.

Shown below are exemplary compounds, compounds 1-10, of this invention.

compound 1

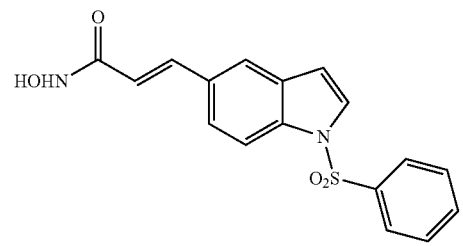

compound 2

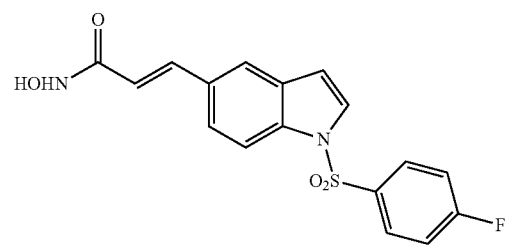

compound 3

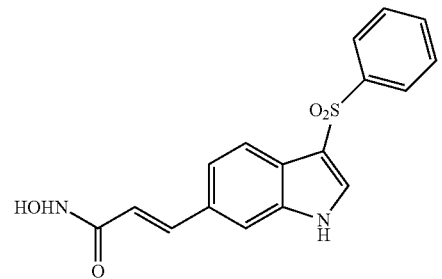

compound 4

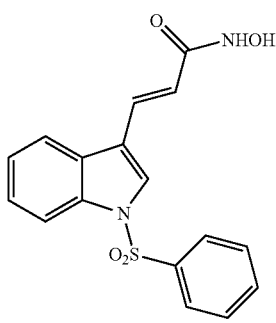

compound 5

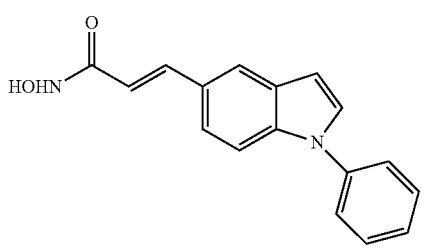

compound 6

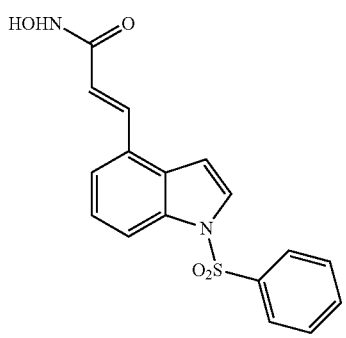

compound 7

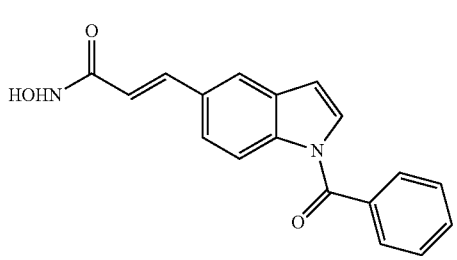

compound 8 compound 9

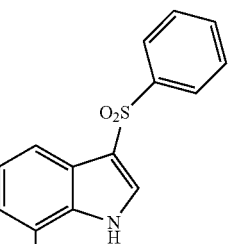

compound 10

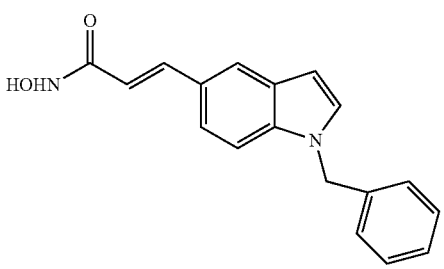

The compounds of this invention, particularly, the compound of formula (I), may be synthesized according to the method described in a U.S. patent application Ser. No. 13/074,312 filed by Chen et al on Mar. 29, 2011; the contents of this prior application is herein incorporated by reference. For example, compound 1 of this invention, 3-(1-benzensulfonyl-1H-indol-5-yl)-N-hydroxy-acrylamide may be synthesized according to Scheme 2 described by Chen et al.

The method of treating heart failure or neuronal injury includes steps of administering to a subject in need thereof an effective amount of the compound of formula (I) as shown above. In a preferred embodiment, the compound is 3-(1-benzensulfonyl-1H-indol-5-yl)-N-hydroxy-acrylamide.

The subject may be a mammal, which includes, but is not limited to, mouse, rat, rabbit, goat, sheep, horse, cow, pig, dog, cat, monkey, chimpanzee, and human. Preferably, the subject is a human. The heart failure is caused by cardiac fibrosis, hypertension, myocardial infarction, myocardial ischaemia, dilated cardiomyopathy, hypertrophic cardiomyopathy, restrictive cardiomyopathy, stress cardiomyopathy, diabetic cardiomyopathy, or idiopathic cardiomyopathy.

In some embodiments, the effective amount of the compound of formula (I) administered to the subject is from about 1 to 100 mg/Kg body weight of the subject by injection, such intravenous or intramuscular injection. The amount is administered to the subject by intravenous injection at about 10, 20, 30, 40, 50, 60, 70, 80, 90 or 100 mg/Kg body weight of the subject, preferably about 30 to 70 mg/Kg body weight of the subject, such as 30, 40, 50, 60 or 70 mg/Kg body weight of the subject. The dose can be administered in a single aliquot, or alternatively in more than one aliquot.

In some embodiments, the method further comprises administering to the subject an agent that is known to improve the cardiac function(s) or the symptoms of neuronal injury before, together with and/or after administering the compound having the formula shown above. Agents that may improve or restore cardiac function(s) include, but are not limited to, angiotensin converting enzyme (ACE) inhibitors, angiotensin II receptor blockers (ARBs), diuretics, digitalis glycosides, beta blockers, direct acting vasodilators, and the like. Examples of ACE inhibitors include, but are not limited to, captopril, enalapril, lisinopril, ramipril, and the like. Examples of ARBs include, but are not limited to, valsartan, telmisarta, losartan, irbesartan, azilsartan, olmesartan, and the like. Examples of diuretics include, but are not limited to, furosemide, bumetanide, torsemide, hydrochlorothiazide, metolazone, spironolactone, and the like. Examples of digitalis glycosides include, but are not limited to, digitoxin, digoxin, lanoxin and the like. Examples of beta blockers include, but are not limited to, acebutolol, bisoprolol, esmolol, propranolol, atenolol, labetalol, carvedilol, metoprolol, nebivolol, bucindolol, and the like. Examples of direct acting vasodilators include, but are not limited to, hydralazine, isosorbide dinitrate and the like. Agents that may improve the symptoms of neuronal injury include, but are not limited to, reactive oxygen scavenger (ROS), anticoagulant, and the like. Examples of reactive oxygen scavenger include, but are not limited to, catalase, superoxide dismutase (SOD), alpha-phenyl-N-tert-butylnitrone (PBN), vitamine E, vitamine C, polyphenolic compounds, carotenoids, and the like. Examples of anticoagulant include, but are not limited to, vitamine K, warfarin, acenocoumarol, heparin, aspirin, clopidogrel, dipyridamole, and the like.

This disclosure also provides a pharmaceutical composition for treating a subject suffering from heart failure or neuronal injury; the composition comprises a therapeutically effective amount of a compound having formula (I) as shown above; and a therapeutically acceptable excipient. In one embodiment, the pharmaceutical composition may be a veterinary medicine for treating a non-human mammal suffering from heart failure or neuronal injury.

Generally, the compound having formula (I) of this invention is present at a level of about 0.1% to 99% by weight, based on the total weight of the pharmaceutical composition. In some embodiments, the compound having formula (I) of this invention is present at a level of at least 1% by weight, based on the total weight of the pharmaceutical composition. In certain embodiments, the compound having formula (I) is present at a level of at least 5% by weight, based on the total weight of the pharmaceutical composition. In still other embodiments, the compound having formula (I) is present at a level of at least 10% by weight, based on the total weight of the pharmaceutical composition. In still yet other embodiments, the compound having formula (I) is present at a level of at least 25% by weight, based on the total weight of the pharmaceutical composition.

In some embodiments, the medicament of said pharmaceutical composition of this invention further includes an agent that is known to improve the function(s) of heart or symptoms of neuronal injury. Examples of agents that are known to improve the function(s) of heart include, but are not limited to, angiotensin converting enzyme (ACE) inhibitors, angiotensin II receptor blockers (ARBs), diuretics, digitalis glycosides, beta blockers, direct acting vasodilators, and the like. Examples of ACE inhibitors include, but are not limited to, captopril, enalapril, lisinopril, ramipril, and the like. Examples of ARBs include, but are not limited to, valsartan, telmisarta, losartan, irbesartan, azilsartan, olmesartan, and the like. Examples of diuretics include, but are not limited to, furosemide, bumetanide, torsemide, hydrochlorothiazide, metolazone, spironolactone, and the like. Examples of digitalis glycosides include, but are not limited to, digitoxin, digoxin, lanoxin and the like. Examples of beta blockers include, but are not limited to, acebutolol, bisoprolol, esmolol, propranolol, atenolol, labetalol, carvedilol, metoprolol, nebivolol, bucindolol, and the like. Examples of direct acting vasodilators include, but are not limited to, hydralazine, isosorbide dinitrate and the like. Examples of agents that are known to improve the symptoms of neuronal injury, include, but are not limited to, reactive oxygen scavenger (ROS), anticoagulant, and the like. Examples of reactive oxygen scavenger include, but are not limited to, catalase, superoxide dismutase (SOD), alpha-phenyl-N-tert-butylnitrone (PBN), vitamine E, vitamine C, polyphenolic compounds, carotenoids, and the like. Examples of anticoagulant include, but are not limited to, vitamine K, warfarin, acenocoumarol, heparin, aspirin, clopidogrel, dipyridamole, and the like.

The medicament or said pharmaceutical composition is prepared in accordance with acceptable pharmaceutical procedures, such as described in Remington's Pharmaceutical Sciences, 17th edition, ed. Alfonoso R. Gennaro, Mack Publishing Company, Easton, Pa. (1985). Pharmaceutically acceptable excipients are those that are compatible with other ingredients in the formulation and biologically acceptable.

The compounds of this invention (e.g., the compound having formula (I) as shown above) may be administered orally, parenterally, transdermally, rectally or by inhalation, alone or in combination with conventional pharmaceutically acceptable excipients. In preferred embodiments, the compounds of this invention are administered parenterally to the subject.

The compounds of the present invention may be formulated into liquid pharmaceutical compositions, which are sterile solutions, or suspensions that can be administered by, for example, intravenous, intramuscular, subcutaneous, or intraperitoneal injection. Suitable diluents or solvent for manufacturing sterile injectable solution or suspension include, but are not limited to, 1,3-butanediol, mannitol, water, Ringer's solution, and isotonic sodium chloride solution. Fatty acids, such as oleic acid and its glyceride derivatives are also useful for preparing injectables, as are natural pharmaceutically-acceptable oils, such as olive oil or castor oil. These oil solutions or suspensions may also contain alcohol diluent or carboxymethyl cellulose or similar dispersing agents. Other commonly used surfactants such as Tweens or Spans or other similar emulsifying agents or bioavailability enhancers that are commonly used in manufacturing pharmaceutically acceptable dosage forms can also be used for the purpose of formulation. Oral administration may be either liquid or solid composition form. Solid dosage forms for oral administration include capsules, tablets, pills, powders, granules, gels, and pastes. In such solid dosage forms, the active compound is mixed with at least one conventional inert diluents such as cellulose, silica, sucrose, lactose, starch or modified starch. Such dosage form can also comprise, as in normal particle, additional substances other than inert diluents, e.g., conventional lubricating agents such as magnesium stearate; or conventional buffering agents. Tablets and pills can additionally be prepared with conventional enteric coatings.

According to some embodiments of the present disclosure, the solid dosage form may be formulated into a bolus for veterinary use. In the field of veterinary medicine, the bolus typically refers to a large pill (≥5 g), or a solid ready-to-swallow pharmaceutical preparation, which may be administered orally. In a preferred embodiment, the bolus contains a sufficient amount of the compound having formula (I) or a pharmaceutical acceptable salt thereof. Thus, the bolus preferably includes at least 100 mg, more preferably at least 1,000 mg, and even more preferably at least 1,500 mg of the compound having formula (I). From a practical perspective, the pharmaceutical composition for veterinary use may contain, for example, between 1,000 to 5,000 mg of the compound having formula (I).

The medicament or said pharmaceutical compositions of this invention may be formulated into a variety of dosage forms for topical application. A wide variety of dermatologically acceptable inert excipients well known to the art may be employed. The topical compositions may include liquids, creams, lotions, ointments, gels, sprays, aerosols, skin patches, and the like. Typical inert excipients may be, for example, water, ethyl alcohol, polyvinyl pyrrolidone, propylene glycol, mineral oil, stearyl alcohol and gel-producing substances. All of the above dosages forms and excipients are well known to the pharmaceutical art. The choice of the dosage form is not critical to the efficacy of the composition described herein.

The medicament or said pharmaceutical compositions of this invention may also be formulated in a variety of dosage forms for mucosal application, such as buccal and/or sublingual drug dosage units for drug delivery through oral mucosal membranes. A wide variety of biodegradable polymeric excipients may be used that are pharmaceutically acceptable, provide both a suitable degree of adhesion and the desired drug release profile, and are compatible with the active agents to be administered and any other components that may be present in the buccal and/or sublingual drug dosage units. Generally, the polymeric excipient comprises hydrophilic polymers that adhere to the wet surface of the oral mucosa. Examples of polymeric excipients include, but are not limited to, acrylic acid polymers and copolymers; hydrolyzed polyvinylalcohol; polyethylene oxides; polyacrylates; vinyl polymers and copolymers; polyvinylpyrrolidone; dextran; guar gum; pectins; starches; and cellulosic polymers.

Accordingly, this invention also provides methods of treating heart failure or neuronal injury in mammals, preferably humans. The method comprises the administration of the medicament or said pharmaceutical composition of this invention that contains a compound having formula as shown above. Such medicament or composition is administered to a mammal, preferably human, by any route that may effectively transports the active ingredient(s) of the composition to the appropriate or desired site of action, such as oral, nasal, pulmonary, transdermal, such as passive or iontophoretic delivery, or parenteral, e.g., rectal, depot, subcutaneous, intravenous, intramuscular, intranasal, intra-cerebella, ophthalmic solution or an ointment. Further, the administration of the compound of this invention with other active ingredients may be concurrent or simultaneous.

It will be appreciated that the dosage of compounds of the present invention will vary from patient to patient not only for the particular compound or composition selected, the route of administration, and the ability of the compound (either alone or in combination with one or more drugs) to elicit a desired response in the patient, but also factors such as disease state or severity of the condition to be alleviated, age, sex, weight of the patient, the state of being of the patient, and the severity of the pathological condition being treated, concurrent medication or special diets then being followed by the patient, and other factors which those skilled in the art will recognize, with the appropriate dosage ultimately being at the discretion of the attendant physician. Dosage regimens may be adjusted to provide the improved therapeutic response. A therapeutically effective amount is also one in which any toxic or detrimental effects of the compound or composition are outweighed by the therapeutically beneficial effects. Preferably, the compounds or compositions of the present invention are administered at a dosage and for a time such that the number and/or severity of the symptoms are decreased.

For convenience, certain terms employed in the context of the present disclosure are collected here. Unless defined otherwise, all technical and scientific terms used herein have the same meaning as commonly understood by one of the ordinary skill in the art to which this invention belongs.

The singular forms "a", "and", and "the" are used herein to include plural referents unless the context clearly dictates otherwise.

The term "alkyl" refers to a straight or branched monovalent hydrocarbon containing 1-20 carbon atoms (e.g., C1-C10). Examples of alkyl include, but are not limited to, methyl, ethyl, n-propyl, i-propyl, n-butyl, i-butyl and tert-butyl. The term "alkenyl" refers to a straight or branched monovalent hydrocarbon containing 2-20 carbon atoms (e.g., C2-C10) and one or more double bonds. Examples of alkenyl include, but are not limited to, ethenyl, propenyl, allyl, and 1,4-butadienyl. The term "alkynyl" refers to a straight or branched monovalent hydrocarbon containing 2-20 carbon atoms (e.g., C2-C10) and one or more triple bonds. Examples of alkynyl include, but are not limited to, ethynyl, 1-propynyl, 1- and 2-butynyl and 1-methyl-2-butynyl. The term "alkoxyl" refers to an —O-alkyl radical. Examples of alkoxyl include, but are not limited to, methoxy, ethoxy, n-propoxy, isopropoxy, n-butoxy, iso-butoxy, sec-butoxy, and tert-butoxy.

The term "aryl" refers to a monovalent 6-carbon monocyclic, 10-carbon monocyclic, 14-carbon tricyclic aromatic ring system. Examples of aryl groups include, but are not limited to, phenyl, naphthyl, and antracenyl. The term "heteroaryl" refers to a monovalent aromatic 5-8 membered monocyclic, 8-12 membered bicyclic, or 11-14 membered tricyclic ring system having one or more heteroatoms (such as O, N, S, or Se). Examples of heteroaryl groups include, but are not limited to, pyridyl, furyl, imidazolyl, benzimidazolyl, pyrimidinyl, thienyl, quinolinyl, indolyl, tetrazol, and thiazolyl.

Alkyl, alkenyl, alkynyl, aryl, and heteroaryl mentioned above include both substituted and unsubstituted moieties. Possible substituents on aryl and heteroaryl include, but are not limited to, C1-C10 alkyl, C2-C10 alkenyl, C2-C10 alkynyl, The term "treatment" as used herein includes preventative (e.g., prophylactic), curative or palliative treatment; and "treating" as used herein also includes preventative (e.g., prophylactic), curative or palliative treatment.

The term "therapeutically effective amount" as used herein refers to an amount effective, at dosages, and for periods of time necessary, to achieve the desired therapeutically desired result with respect to the treatment of heart failure or neuronal injury.

The phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The terms "compounds", "compositions", "active compounds", "agent" or "medicament" are used interchangeably herein to refer to a compound or compounds or composition of which, when administered to a subject (human or animal) induces a desired pharmacological and/or physiological effect by local and/or systemic action.

The term "administered", "administering" or "administration" are used interchangeably herein to refer means either directly administering a compound or a composition of the present invention, or administering a prodrug, derivative or analog which will form an equivalent amount of the active compound within the body.

The term "subject" or "patient" refers to an animal including the human species that is treatable with the compositions and/or methods of the present invention. The term "subject" or "patient" intended to refer to both the male and female gender unless one gender is specifically indicated. Accordingly, the term "subject" or "patient" comprises any mammal which may benefit from treatment of neuronal injury.

The term "improve cardiac function" means that a composition is administered to or a method is used for a subject for a period effective to improve cardiac functions as determined by comparison with cardiac functions in subjects not being administered the composition or using the method. Moreover, "improve" shall also mean to ameliorate the symptoms of heart failure.

The term "restore" refers to a long-term (e.g., as measured in weeks or months) improvement in cardiac functions in a subject, by comparison with cardiac functions in subjects not being administered the composition or using the method.

The present invention will now be described more specifically with reference to the following embodiments, which are provided for the purpose of demonstration rather than limitation.

EXAMPLES

Example 1

Compound 1 Reduces Cardiac Fibrosis in Subject Having Heart Failure

To verify whether compounds of this invention is capable of improving cardiac functions, animals were injected with isoproterenol subcutaneously to induce heart failure and then treated with the test compound (e.g., compound 1) or vehicle, and the effect of the test compound(s) on cardiac function was observed by echocardiography.

1.1 Preparation of Heart Failure Animal Model

Adult male Wistar rats (each weighted about 240-270 g, and were purchased from BioLASCO Taiwan Co., Ltd) were used in this study. Animals were randomly assigned to "HF+vehicle" or "HF+compound 1" group. Heart failure (HF) rats received one subcutaneous injection of isoproterenol at a dosage of 100 mg/Kg. They were housed in an animal room under temperature control (24-25° C.) and 12:12 light-dark cycle. Standard laboratory rat chow and tap water were available ad libitum. All animal experiments were carried out in accordance with the guidelines established by the Institutional Animal Care and Utilization Committee of the Taipei Medical University (Taipei, Taiwan, R.O.C.).

1.2 Preparation and Administration of Medicament

Compound 1 was dissolved in 0.4% carboxymethylcellulose with a final concentration of 100 mg/ml.

One week after isoproterenol administration, heart failure rats were further randomly assigned to receive compound 1 (100 mg/kg) or the vehicle (0.4% carboxymethylcellulose) by oral gavage once daily for 7 days Then, the rats were anesthetized with an i.p. injection of sodium pentobarbital (100 mg/kg, Sigma). A midline thoracotomy was then performed, and the heart was removed, weighed, and dissected from each rat for further analysis.

1.3 Echocardiography

Echocardiograms were performed before the animals were euthanized, using HP Sonos 5500 system with a 15-6L probe (6 to 15 MHz, SONOS 5500, Agilent Technologies, Palo Alto, Calif.) or Vivid I ultrasound cardiovascular system (GE Healthcare, Haifa, Israel). LV end-diastolic diameter (LVEDD), LV end-systolic diameter (LVESD), and wall thickness were measured from M-mode tracings. The LV fractional shortening percentage was calculated as ([LVEDD-LVESD]/LVEDD)×100. The LV ejection fraction was calculated by Techholz's formula.

Results are summarized in Table 1. All quantitative data are expressed as the mean±S.E.M, and un-paired T test was used to compare the differences between groups. Values are expressed as mean±S.E.M, *$P<0.05$ compared to before and after treatment of the same group, #$P<0.05$ compared to vehicle and compound 1 group of the same treatment.

TABLE 1

Echocardiography in HF rats treated with or without compound 1

| Treatment | Group | |
| --- | --- | --- |
| | HF + vehicle (n = 7) | HF + compound 1 (n = 7) |
| Before treatment | | |
| IVSd (mm) | 1.4 ± 0.1 | 1.4 ± 0.1 |
| LVEDd (mm) | 5.4 ± 05 | 5.4 ± 0.4 |
| LVESd (mm) | 3.5 ± 0.4 | 3.4 ± 0.3 |
| Ejection fraction (%) | 69 ± 4 | 68 ± 2 |
| Fraction shortening (%) | 37 ± 4 | 38 ± 3 |
| After treatment | | |
| IVSd (mm) | 1.4 ± 0.1 | 1.3 ± 0.1 |
| LVEDd (mm) | 5.6 ± 0.3 | 4.6 ± 0.2*# |
| LVESd (mm) | 3.9 ± 0.3 | 2.4 ± 0.2*# |
| Ejection fraction (%) | 59 ± 3 | 81 ± 3*# |
| Fraction shortening (%) | 30 ± 3 | 47 ± 3*# |

In cardiovascular physiology, ejection fraction is the fraction of blood pumped out of the right and left ventricles with each heart beat. Damage to the muscle of the heart, such as that sustained during myocardial infarction or in cardiomyopathy, impairs the heart's ability to eject blood and therefore reduces ejection fraction. Therefore, reduction in the ejection fraction is often observed in subjects suffering from heart failure. Heart failure rats that received compound 1 (100 mg/Kg) exhibited marked increase in ejection fraction (EF=81%) as compared with heart failure rats treated with vehicle (EF=59%). Hydralazine, a clinically available drug for treating heart failure, was also used in the present animal model. One week after heart failure induction by one subcutaneous injection of isoproterenol (150 mg/kg), hydralazine (10 mg/kg) was administered by intraperitoneally (i.p.) once daily for 7 days. The results indicated that hydralazine increased the ejection fraction from 59±4% to 76±10% (data not shown).

These results indicate that compound 1 of this invention is efficacious in improving cardiac functions.

1.4 Morphology Histological Analysis

FIG. 1 depicts the cardiac morphology taken from control rat, and HF rat treated with vehicle or compound 1. The upper-panel photographs illustrate the frontal view of the heart. The white color changes indicated the existence of cardiac fibrosis. It is noted that the HF rat treated with vehicle exhibited severe cardiac fibrosis, as compared to the control rat or rat that was treated with compound 1. The lower panels are photographs taken from the isolated heart chambers from interventricular septum. Significant white color changes were found in left ventricular apex in HF+vehicle rat, but not in control rat and HF+compound 1 rat.

Figure 2:
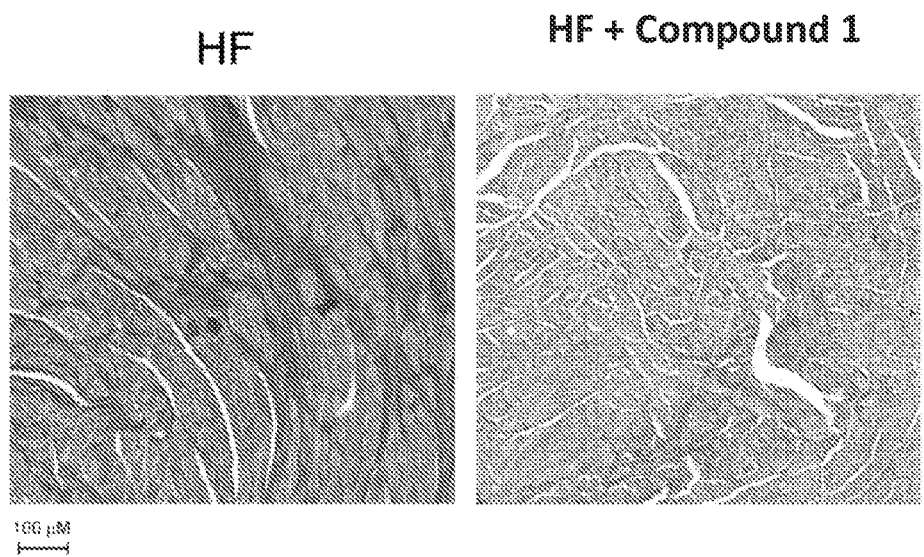
FIG. 2 presents photographs illustrating collagen disposition stained with Masson's trichrome of apex from HF rat treated with vehicle or compound 1 of this invention in accordance with one example of the present invention.

Left ventricular apex prepared from heart failure rats treated with or without compound 1 were fixed in formalin and embedded with paraffin. Tissues were stained with Masson trichrome for the visualization of interstitial collagen deposition. FIG. 2 depicts the collagen depositions in HF rat treated with vehicle or compound 1, where the blue color indicates the cardiac fibrosis. Histomorphological examination revealed that HF rat treated with compound 1 developed less cardiac fibrosis than that treated with vehicle.

In view of the foregoing, compound 1 of this invention significantly improves cardiac functions in heart failure animal model. Specifically, the present compound 1 is efficacious in increasing the ejection fraction of the heart, and in decreasing the incidence of cardiac fibrosis. Such findings confirm our proposition that compound 1 may improve or restore cardiac functions in subjects suffering from heart failure.

Example 2

Compound 1 Reduces Cardian ANP Expression

In this example, the expression of atrial natriuretic peptide (ANP) is investigated to elucidate the effect of compounds of this invention on the expression thereof.

Figure 3:
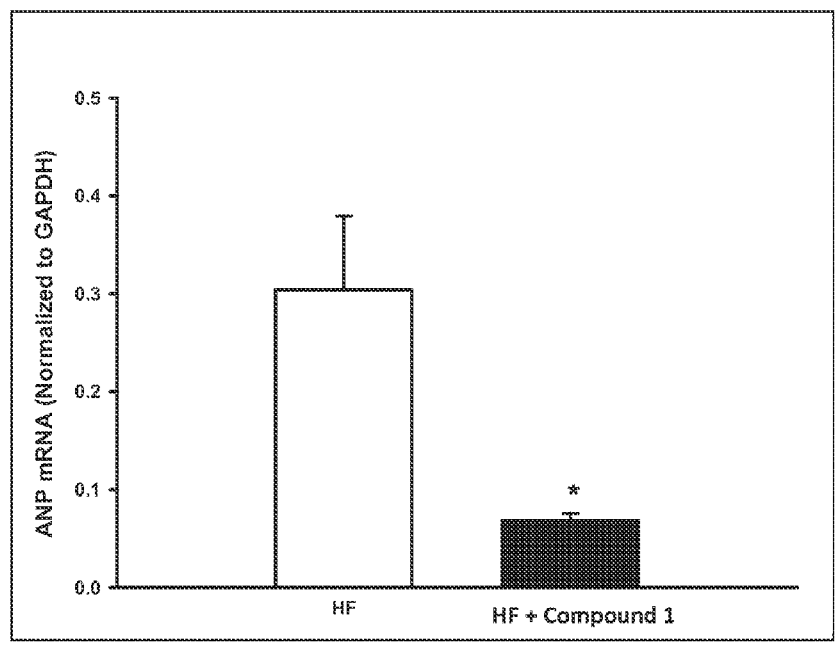
FIG. 3 is a bar diagram illustrating cardiac ANP expression in HF rat treated with vehicle or compound 1 of this invention in accordance with one example of the present invention.

The preparation and administration of medicament were carried out as described above. Total RNA was extracted from tissues by using TRIzol reagent. The total RNA was reverse-transcribed with random primers (Invitrogen, Carlsbad, USA) and superscript III cDNA synthesis kit (Invitrogen) according to the manufacturer's instructions (Invitrogen, Carlsbad, USA). The RNA expression of ANP and GAPDH was carried out by using a SYBER Green-based qPCR with an ABI PRISM7300 system (Applied Biosystems, Foster City, USA). Primers and probes were designed using Primer Express 2.0 (Applied Biosystems). Threshold cycle ($C_t$) values for all genes were normalized with their respective $C_t$ values to GAPDH RNA expression by using the $2^{(-\Delta\Delta Ct)}$ method. Results are depicted in FIG. 3.

ANP is a polypeptide hormone secreted by heart muscle cells. It is released by muscle cells in the atria of the atrial myocytes in response to high blood pressure. Therefore, ANP is a clinical and functional parameter of heart failure. Results depicted in FIG. 3 indicate that the oral intake of compound 1 (100 mg/kg) for a week significantly decreased cardiac ANP mRNA in heart failure rats as compared to those with vehicle. Accordingly, compound 1 of this invention significantly improves cardiac functions in heart failure animal model.

Example 3

Compound 1 Provides Neuronal Protective Activity to Subjects Suffering from Brain Injury 3.1 Preparation of Traumatic Brain Injury (TBI) Animal Model To varify whether compounds of this invention possess any neuron protective effects, animals were artificially induced to produce TBI and then treated with the test compound (e.g., compound 1 or valproic acid) or vehicle, and the effect of the test compound(s) on brain contusion area and behaviour function deficit were respectively measured by TTC staining and behaviour test (e.g., skilled forelimb reaching task).

Adult male Sprague-Dawley rats (each weighted about 250-300 g, and were purchased from BioLASCO Taiwan Co., Ltd) were used in this study. The rats were randomly allocated into three groups: (i) TBI+test Compound (e.g., Compound 1 or valproic acid (VPA)), (ii) TBI+VEH (i.e., vehicle-treated TBI rats), and (iii) Sham (sham-operated control). They were housed in an animal room under temperature control (24-25) and 12:12 light-dark cycle. Standard laboratory rat chow and tap water were available ad libitum. All animal experiments were carried out in accordance with the guidelines established by the Institutional Animal Care and Utilization Committee of the Taipei Medical University (Taipei, Taiwan, R.O.C.).

Surgical anesthesia was induced by ketamine (90 mg/kg body weight) and xylazine (10 mg/kg body weight), which were administered intraperitoneally (ip). Following anesthesia, the animals were secured in a stereotaxic frame and ventilated mechanically. A cortical contusion was produced on the exposed cortex using a controlled impactor device TBI-0200 TBI Model system (Precision Systems and Instrumentation). The scalp and epicranial aponeurosis were retracted, and a 3 mm diameter circular craniotomy was performed with a burr drill, lateral to the mid-sagittal suture (contralateral to preferred limb), with the center at the following coordinates: AP=+1 mm, ML=±2.5 mm from bregma. Briefly, the impacting shaft was extended, and the impact tip was centered and lowered over the craniotomy site until it touched the dura mater. Then, the rod was retracted and the impact tip was advanced farther to produce a brain injury of moderate severity for rats (tip diameter, 3 mm; cortical contusion depth, 2 mm; impact velocity, 4 m/sec). The impact tip was wiped clean with sterile alcohol after each impact and cleaned/disinfected further with cidex after surgery. Core temperature was maintained at 37±0.5° C. with a heating pad during surgery. Immediately after injury, the skin incision was closed with nylon sutures.

3.2 Preparation and Administration of Medicament

Compound 1 was dissolved in 5% ethanol, 35% polyethylene glycol and 60% normal saline at a concentration of 15 mg/ml. All test animals received intravenous injection of either compound 1 (30 mg/Kg), valproic acid (VPA, 30 mg/kg) or vehicle (5% ethanol, 35% polyethylene glycol and 60% normal saline) at 0-7 days after TBI.

3.3 Sample Preparation

Animals were deep anesthetized with choral hydrate (400 mg/kg) and perfused with both normal saline and 4% paraformaldehyde. With the removed brain, the biopsy (2 mm in thickness) spanning the rostral-caudal extent was sectioned for following measurement of cortical tissue loss. Acquisition of image with arranged brain slices was fulfilled via a scanner (HP photosmart B110a, 600 dpi).

3.4 Contrusion Volume Measurement

Figure 4:
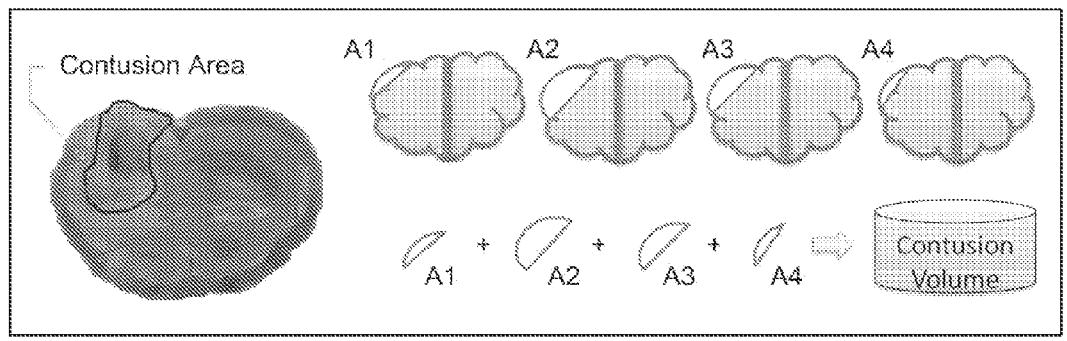
FIG. 4 is a schematic presentation that illustrates how the contusion volume is estimated in accordance with one example of this invention.

Considering the possible differential shrinkage resulting from excision and fixation, the amount of cortical damage could be estimated as a part of the total cortical volume. In this study, the "contusion ratio" was defined as the correlation between contusion volume and ipsilateral brain. To generate the contusion ratio for each slice, both the area of contusion volume ($c_{area}$) and ipsilateral brain ($b_{area}$) was manual outlined and characterized by the number of the included pixels. FIG. 4 is a schematic presentation of the estimation of the contusion volume. Briefly, to describe the entire contusion volume for further analysis, the areas of contusion volume was particularly analyzed. The contusion volume in a single slice having a thickness of 2 mm is defined as $0.5 \times (Area_{front} + Area_{back}) \times 2$, hence the entire contusion volume is expressed as $0.5 \times (A_1 + A_2) \times 2 + 0.5 \times (A_2 + A_3) \times 2 + \ldots + 0.5 \times (A_{N-1} + A_N) \times 2$. The expression can be rewritten into the following equation, $$\text{Contusion volume} = (2 \times \Sigma_{n=1}^{N} A_N) - (A_1 + A_N)$$

3.5 2,3,5-Triphenyltetrazolium Chloride (TTC) Staining

The TTC staining was used to assess the lesion size by comparing different viability of neuronal tissues. The excised brain was sliced to 2 mm-thick sections and incubated in 1% TTC solution for 30 minutes at 37° C. In viable neuronal tissues, dehydrogenase enzymes converted TTC to a red formazan pigment that stains tissue dark red. The damaged tissues stained a pale-white color since they lacked dehydrogenase enzymes with which TTC reacted.

Figure 5:
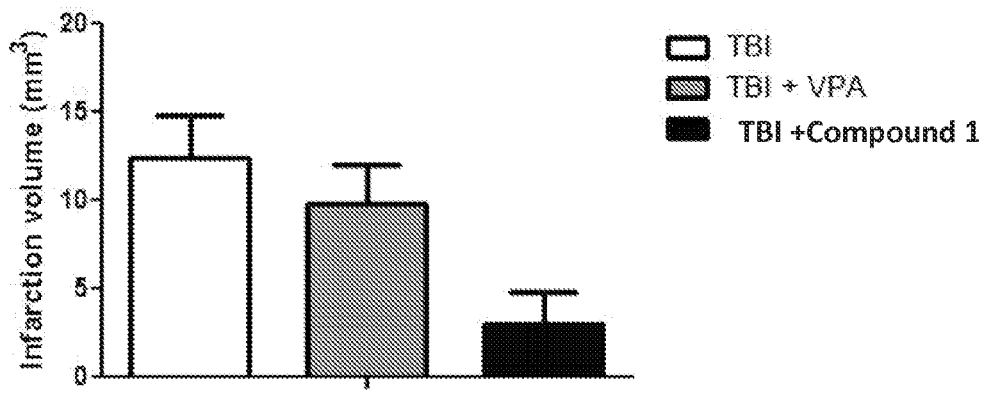
FIG. 5 illustrates the effect of compound 1 or VPA on the reduction of the contusion area caused by TBI in accordance with one example of this invention.

FIG. 5 depicts the effect of test compounds, such as compound 1 or VPA, on reduction of the contrusion area caused by TBI. It is evident from FIG. 5 that compound 1 of this invention is more effective in diminishing the area of damaged brain tissues as compared with that of valproic acid (VPA), which is a chemical known as histone deactylase (HDAC) inhibitor and has ben used to control seizure.

3.6 Training/Behavioral Testing

All test animals were trained to criterion on the skilled forelimb reaching task. Animals then underwent TBI surgery, after which they were allocated to different experimental groups as described above. Each animal was tested for the skilled forelimb reaching task on the first, third, and seventh days postoperatively and then weekly for 6 weeks. On days when test compound (e.g., compound 1 or VPA) or vehicle was administered (i.e., Day 1, 3, or 7), all behavior testing was performed before drug injection. Skilled forelimb reaching was tested as previously described. Briefly, animals were placed in a transparent Plexiglas chamber (30 cm×36 cm×30 cm) and trained to reach through a window (1.5 cm×3 cm) to retrieve small sucrose pellets (45 mg; Bilaney Consultants, Frenchtown, N.J.) placed on a platform at a distance of 1 cm. During the initial days of training, limb preference was determined and placement of pellets was adjusted to favor the use of the preferred forelimb. Before surgery, baseline performance, which was defined as the average of the last 3 testing sessions of the preoperative testing, was established. Success was defined as an animal grasping the pellet on the first attempt and placing it into the mouth (i.e., "first reach success"). Each testing session consisted of 20 reaching opportunities using the preferred forelimb. Attempts using the non-preferred forelimb were not included in analyses. The preoperative criterion was at least 16 successes in 20 attempts for 3 consecutive days. A maximum time limit of 5 minutes/testing session was given.

3.7 Results

Figure 6:
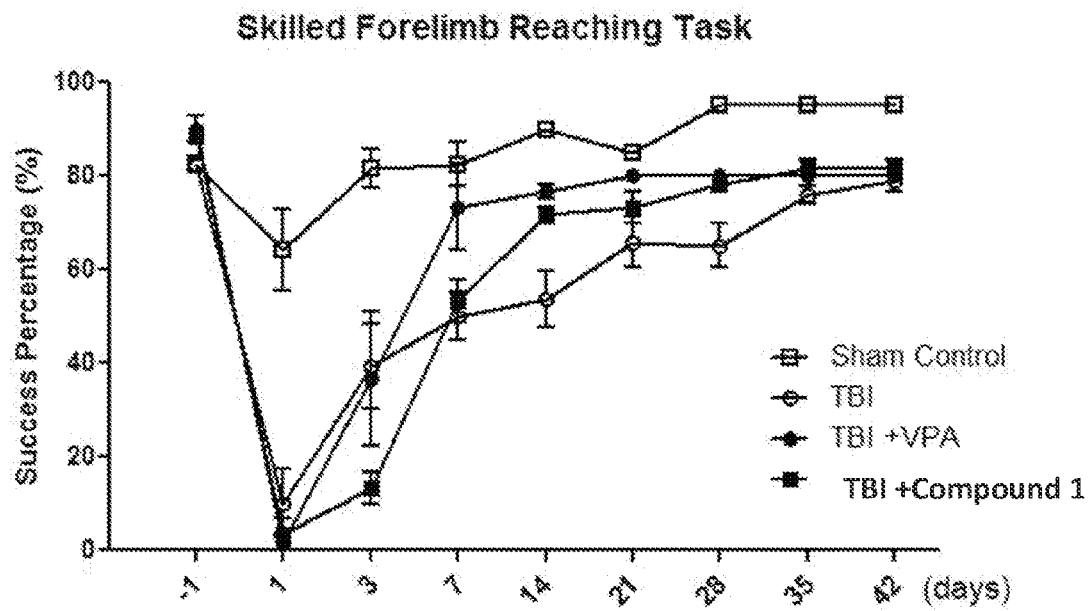
FIG. 6 illustrates the effect of compound 1 or VPA on the improvement of behaviour function task of a TBI subject in accordance with one example of this invention.

Medicaments prepared in accordance with steps described in Example 3.2 were given to the 3 groups of TBI animals of Example 3.1, and these animals were then subjected to the as-described skilled forelimb reaching task, and results are illustrated in FIG. 6. Again, compound 1 of this invention, as well as VPA, significantly improve the behaviour function deficits caused by TBI, such findings confirm our proposition that compound 1 may provide neuronal protective activity to subjects suffering from brain injury.

Example 4

Compound 1 Provides Neuronal Protective Activity to Subjects Having Ischematic Stroke In this example, effects of compounds of this invention were varified using ischematic stroke animal model. Similar to procedures described in Example 3, animals were artificially induced to produce ischematic stroke and then treated with the test compound (e.g., compound 1 or valproic acid) or vehicle, and the effect of the test compound(s) on infraction area and up-regulation of cAMP response element-binding protein (CREB) were respectively measured by TTC staining and western blot analysis.

4.1 Preparation of Middle Cerebral Artery Occlusion (MCAO) Animal Model (or Ischemic Stroke Rat Model)

Middle cerebral artery (MCA) occlusion is achieved in this animal model by ligating the ends of inferior cerebral veins of the tested rats so as to simulate the condition of ischemic stroke. Briefly, approaching the right MCA by a temporal incision and thereby exposing the right MCA at the level of the inferior cerebral vein. The bilateral common carotid arteries were isolated through a neck incision and occluded with aneurysm clips. The MCA was then occluded by 10-0 Nylon ligation just distal to the inferior cerebral vein. After 60 minutes, rats were re-anesthetized, the carotid clips were removed, and the neck incision was closed. The rats were returned to their home cage after fully recovered from anesthesia. The sham surgery is similar to the MCAO surgery, which included the step of opening the dura, yet without the steps of isolating, clipping, or coagulating neither the MCA nor carotid vessel.

4.2 Preparation and Administeration of Medicament

Compound 1 was dissolved in 5% ethanol, 35% polyethylene glycol and 60% normal saline at a concentration of 15 mg/ml. All test animals received intravenous injection of either compound 1 (30 mg/Kg), valproic acid (VPA, 30 mg/kg) or vehicle (5% ethanol, 35% polyethylene glycol and 60% normal saline) at 0-7 days after MCAO.

4.3 Western Blot Analysis of CREB

Collected protein samples were mixed with Laemli sample buffer. The sample buffer was resolved onto SDS-polyacrylamide gels and transferred to nitrocellulosemembranes while membranes were blocked with 5% milk, 0.05% Tween-20 in phosphate (PBS) followed by overnight incubation with the corresponding primary antibodies and buffers. Following the wash in PBS/Tween-20 and PBS, immunolabeled protein bands including histone deacetylase inhibitor 1 (HDAC1), histone deacetylase inhibitor 2 (HDAC2), acetylated histone H2A (Ac-H2A), acetylated histone H2B (Ac-H2B), phosphorylation of cAMP response element-binding protein (p-CREB), and total protein of cAMP response element-binding protein (t-CREB) expressed at right anterior brain (RA), right posterior brain (RP), left anterior brain (LA), and left posterior brain (LP) were respectively detected by using HRP-conjugatedanti-rabbit, anti-mouse or anti-goat antibody (Santa CruzBiotechnology; dilution 1:5,000) with both chemiluminiscence system (ECL, GE Healthcare Bioscience, Buckinghamshire, UK), and autoradiographic exposure to HyperfilmTMECL (GE Healthcare Bioscience). The Immunoblottingquantification was fulfilled via Quantity OneTMsoftware (Bio-Rad).

4.4 Results

Figure 7A:
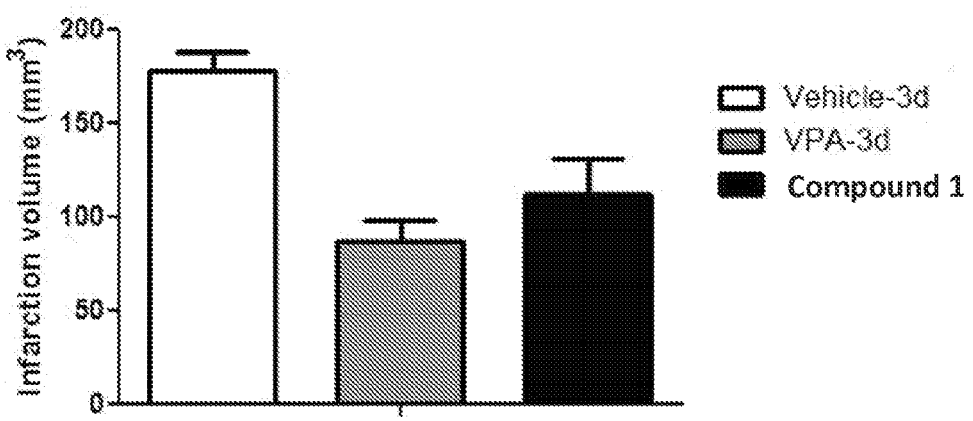
FIG. 7A illustrates the infarction area of MCAO rats treated with compound 1 or VPA for 30 min, in accordance with one example of this invention.
Figure 7A:
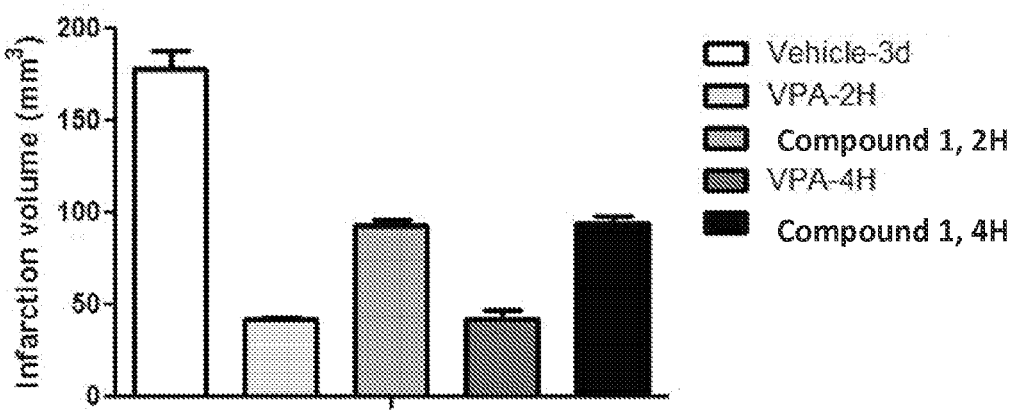
Figure 7B:
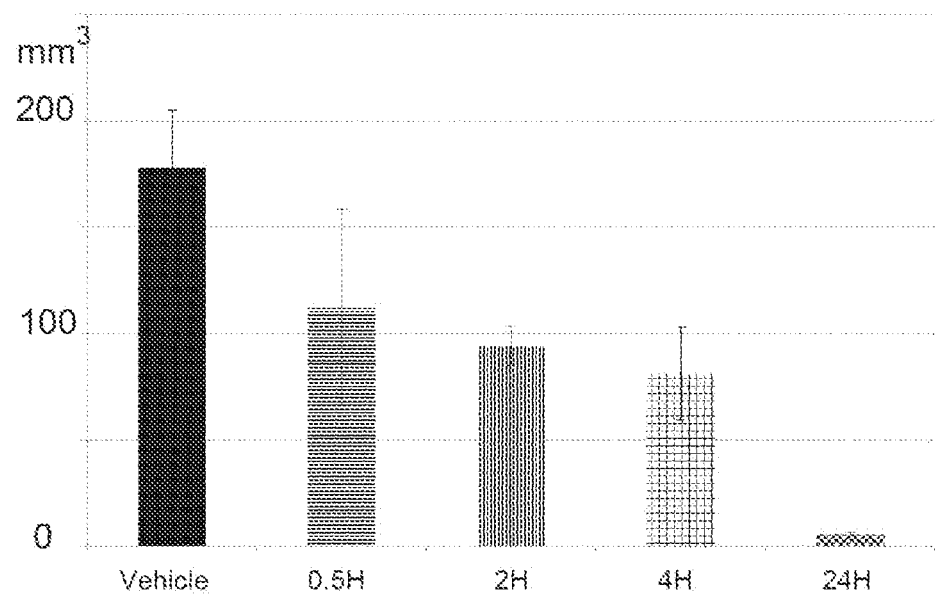
FIG. 7B illustrates the infarction area of MCAO rats respectively treated with Compound 1 for 30 min, 2 hours, 4 hours and 24 hours in accordance with one example of this invention.

Medicaments prepared in accordance with steps described in Example 4.2 were given to the 3 groups of MCAO rats of Example 4.1 (N=5, for each group), and the infraction area of these animals were then stained and estimated by similar steps described in Examples 3.4 and 3.5, and results are illustrated in FIGS. 7A and 7B. Infarction volume in three treatment windows, i.e., 30 min, 2 hours and 4 hours after stroke, were respectively measured; and significant reduction of infarction volume was noted on the treatment window of 3 days after compound 1 and/or VPA treatment in MCAO rats (FIG. 7A). In another example, after induction of MACO, rats were infused with compound 1 at 30 min, 2 hrs, 4 hrs, and 24 hrs, respectively; and the infarction volume was calculated 3 days after MCAO. The results confirmed that treatment of compound 1 may significantly reduce infraction volume even 24 hrs after MCAO (FIG. 7B).

Figure 8:
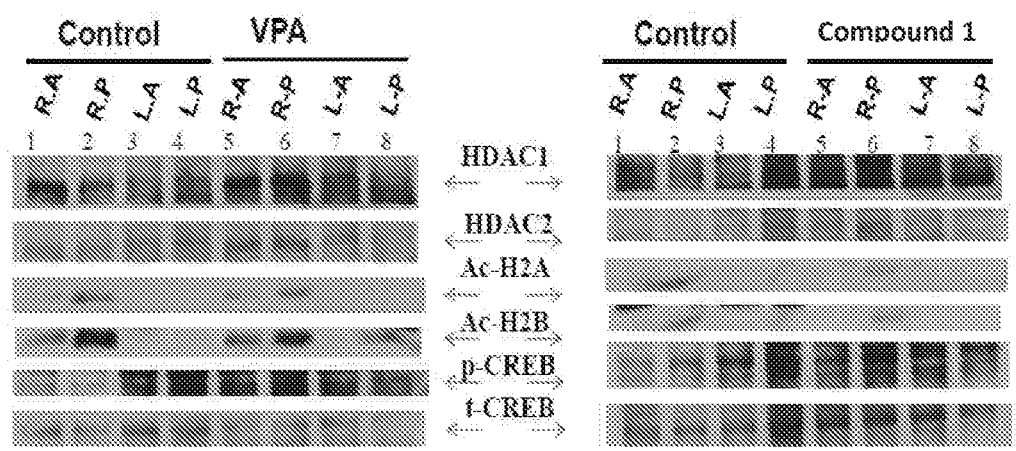
FIG. 8 illustrates the up-regulation of cAMP response element-binding protein (CREB) in MCAO rats treated with either VPA or Compound 1 in accordance with one example of this invention.

As indicated above, cerebral ischemia triggers robust phosphorylation of cAMP response element-binding protein (CREB) and CREB-mediated gene expression encoding neuroprotective molecules in neurons (Kitagawa K., FEBS J. 2007 274(13):3210-7); hence compounds effective in activating phosphorylation of CREB are potential lead compounds that may mitigate ischemia stroke. Level of CREB phosphorylaiton was measured by western blot ananlysis in accordance with steps described in Example 4.3. Results are illustrated in FIG. 8. As is evident from FIG. 8, up-regulation of CREB including phosphorylated CREB (p-CREB) and total CREB (t-CREB), was observed at both right- and left-anterior (RA, LA) and right- and left-posterior (RP, LP) brain areas in rats receiving Compound 1 treatment.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of treating a subject suffering from heart failure or neuronal injury comprising administering to the subject an effective amount of a compound having the following structure,

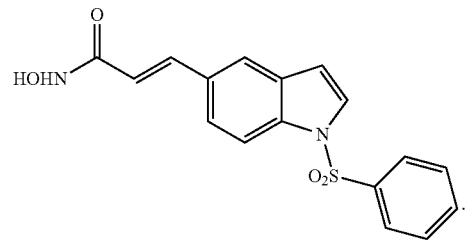

2. The method of claim 1, wherein the subject is a human.

3. The method of claim 1, wherein the heart failure is caused by any of cardiac fibrosis, hypertension, myocardial infarction, myocardial ischaemia, dilated cardiomyopathy, hypertrophic cardiomyopathy, restrictive cardiomyopathy, stress cardiomyopathy, diabetic cardiomyopathy, or idiopathic cardiomyopathy.

4. The method of claim 3, wherein the heart failure is caused by cardiac fibrosis or hypertension.

5. The method of claim 3, wherein the neuronal injury is traumatic brain injury or ischemic stroke.

* * * * *